(12) United States Patent
Beaupré

(10) Patent No.: US 7,285,895 B2
(45) Date of Patent: Oct. 23, 2007

(54) ULTRASONIC MEDICAL DEVICE AND METHOD

(75) Inventor: Jean Beaupré, Cincinnati, OH (US)

(73) Assignee: Crescendo Technologies, LLC, Cincinnati, OH (US)

( * ) Notice: Subject to any disclaimer, the term of this patent is extended or adjusted under 35 U.S.C. 154(b) by 0 days.

(21) Appl. No.: 11/262,353

(22) Filed: Oct. 28, 2005

(65) Prior Publication Data

US 2006/0241471 A1    Oct. 26, 2006

Related U.S. Application Data

(60) Provisional application No. 60/661,739, filed on Mar. 15, 2005.

(51) Int. Cl.
  *H01L 41/08*    (2006.01)
  *H02N 2/00*    (2006.01)
(52) U.S. Cl. .................. 310/323.19; 310/323.02; 310/323.12; 310/325
(58) Field of Classification Search .......... 310/323.01, 310/323.02, 323.09, 323.12, 323.19, 325
See application file for complete search history.

(56) References Cited

U.S. PATENT DOCUMENTS

| | | | |
|---|---|---|---|
| 3,636,943 A | | 1/1972 | Balamuth |
| 4,438,509 A | | 3/1984 | Butler et al. |
| 4,541,429 A | * | 9/1985 | Prosl et al. .................. 604/249 |
| 4,933,590 A | * | 6/1990 | Inoue et al. ............ 310/323.14 |
| 4,965,482 A | * | 10/1990 | Ohnishi et al. ......... 310/323.13 |
| 5,322,055 A | | 6/1994 | Davison et al. |
| 5,324,299 A | | 6/1994 | Davison et al. |
| 5,425,704 A | | 6/1995 | Sakurai et al. |
| 5,508,580 A | * | 4/1996 | Maeno et al. .......... 310/323.13 |
| 5,554,905 A | * | 9/1996 | Gschwind et al. ..... 310/323.02 |
| 5,746,756 A | | 5/1998 | Bromfield et al. |
| 5,798,599 A | | 8/1998 | Harwood |
| 5,828,158 A | * | 10/1998 | Chatellard ................... 310/328 |
| 5,836,897 A | | 11/1998 | Sakurai et al. |
| 5,989,275 A | | 11/1999 | Estabrook et al. |
| 6,491,708 B2 | | 12/2002 | Madan et al. |

FOREIGN PATENT DOCUMENTS

GB           868784         8/1957

* cited by examiner

*Primary Examiner*—Thomas M. Dougherty
(74) *Attorney, Agent, or Firm*—Greenebaum Doll & McDonald PLLC; Glenn D. Bellamy

(57) ABSTRACT

Ultrasonic devices having transducer assembly including a stack of alternating electrodes and piezoelectric elements. A mounting device having a first and second end is adapted to receive ultrasonic vibration from the stack and transmit it from the first to the second end. A bolt including a head and shaft is configured to threadedly engaged the mounting device. The transducer assembly includes a deformable pressure element having a central opening that permits insertion of the shaft therethrough, and has a convex side facing the bolt head and a concave side facing the stack in a non-deformed state, but, in a deformed state, applies compression forces to the stack based on the deformation. The deformable pressure element may alternately include a surface area, in its deformed state, substantially equivalent to the surface area of a piezoelectric element and/or a first and second beveled surface defining the concave side.

6 Claims, 8 Drawing Sheets

ULTRASONIC MEDICAL DEVICE AND METHOD

This application claims the benefit of Provisional Patent Application Ser. No. 60/661,739, filed on Mar. 15, 2005, to which priority is claimed pursuant to 35 U.S.C. §119(e) and which is hereby incorporated herein by reference.

BACKGROUND OF THE INVENTION (a) Field of the Invention

The present invention relates generally to ultrasonic transducer assemblies and, more particularly, to transducer assemblies of the composite or sandwich type incorporating a deformable pressure element.

(b) Description of the Prior Art

Ultrasonic transmission devices are well known for use in a variety of applications such as, for example, surgical operations and procedures. Ultrasonic transmission devices usually include a transducer that converts electrical energy into vibrational motion at ultrasonic frequencies. The vibrational motion is transmitted to vibrate a distal end of a surgical instrument. Such uses are disclosed in representative U.S. Pat. Nos. 3,636,943 and 5,746,756, both incorporated herein by reference.

High-intensity ultrasonic transducers of the composite or sandwich type typically include front and rear mass members with alternating annular piezoelectric transducers and electrodes stacked therebetween. Most such high-intensity transducers are of the pre-stressed type. They employ a compression bolt that extends axially through the stack to place a static bias of about one-half of the compressive force that the piezoelectric (PZT) transducers can tolerate. Sandwich transducers utilizing a bolted stack transducer tuned to a resonant frequency and designed to a half wavelength of the resonant frequency are described in United Kingdom Patent No. 868,784. When the transducers operate they are designed to always remain in compression, swinging from a minimum compression of nominally zero to a maximum peak of no greater than the maximum compression strength of the material.

As shown in FIG. 1, an acoustic or transmission assembly 80 of an ultrasonic device generally includes a transducer stack or assembly 82 and a transmission component or working member. The transmission component may include a mounting device 84, a transmission rod or waveguide 86, and an end effector or applicator 88.

The transducer assembly 82 of the acoustic assembly 80 converts the electrical signal from a generator (not shown) into mechanical energy that results in longitudinal vibratory motion of the end effector 88 at ultrasonic frequencies. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. The transducer assembly 82, which is known as a "Langevin stack", generally includes a transduction portion 90, a first resonator or aft end bell 92, and a second resonator or fore end bell 94. The transducer assembly 82 is preferably an integral number of one-half system wavelengths (nλ/2) in length.

The distal end of the first resonator 92 is connected to the proximal end of transduction section 90, and the proximal end of the second resonator 94 is connected to the distal end of transduction portion 90. The first and second resonators 92 and 94 have a length determined by a number of variables, including the thickness of the transduction section 90, the density and modulus of elasticity of material used in the resonators 92 and 94, and the fundamental frequency of the transducer assembly 82.

The transduction portion 90 of the transducer assembly 82 may include a piezoelectric section ("PZTs") of alternating positive electrodes 96 and negative electrodes 98, with piezoelectric elements 70 alternating between the electrodes 96 and 98. The piezoelectric elements 70 may be fabricated from any suitable material, such as, for example, lead zirconate-titanate, lead meta-niobate, lead titanate, or ceramic piezoelectric crystal material. Each of the positive electrodes 96, negative electrodes 98, and piezoelectric elements 70 have a bore extending through the center. The positive and negative electrodes 96 and 98 are electrically coupled to wires 72 and 74, respectfully. The wires 72 and 74 transmit the electrical signal from the generator to electrodes 96 and 98.

The piezoelectric elements 70 are energized in response to the electrical signal supplied from the generator to produce an acoustic standing wave in the acoustic assembly 80. The electrical signal causes disturbances in the piezoelectric elements 70 in the form of repeated small displacements resulting in large compression forces within the material. The repeated small displacements cause the piezoelectric elements 70 to expand and contract in a continuous manner along the axis of the voltage gradient, producing high frequency longitudinal waves of ultrasonic energy. The ultrasonic energy is transmitted through the acoustic assembly 80 to the end effector 88.

The piezoelectric elements 70 are conventionally held in compression between the first and second resonators 92 and 94 by a bolt and washer combination 106. The bolt 106 preferably has a head, a shank, and a threaded distal end. The bolt 106 is inserted from the proximal end of the first resonator 92 through the bores of the first resonator 92, the electrodes 96 and 98, and piezoelectric elements 70. The threaded distal end of the bolt 106 is screwed into a threaded bore in the proximal end of second resonator 94.

Other embodiments of the prior art utilize a stud that is threadedly engaged with both the first and second resonators 92 and 94 to provide compressive forces to the PZT stack. Threaded studs are also known in the prior art for attaching and detaching transmission components to the transducer assembly. See, for example, U.S. Pat. Nos. 5,324,299 and 5,746,756. Such bolts and studs are utilized to maintain acoustic coupling between elements of the sandwich type transducer or any attached acoustic assembly. Coupling is important to maintain tuning of the assembly, allowing the assembly to be driven in resonance.

In previous designs, the compression means may be inadequate and may be unable to provide a uniform pressure across the inside diameter to the outside diameter of each PZT and through the entire PZT stack, the "r" and "z" axes as shown in FIG. 1 and graphically illustrated in FIG. 2. A Finite Element analysis shows that the ratio of the pressure in the R axis is of the order of 4:1.

U.S. Pat. No. 5,798,599 discloses an ultrasonic transducer assembly which includes soft, aluminum foil washers disposed between facing surfaces of adjacent members of the PZT stack. The washers deform under compressive loading to follow the microscopic surface irregularities of the adjacent member surfaces. However, such washers are used primarily to address local stresses and do not address the macroscopic stress gradients present in loaded ultrasonic instruments.

Current designs, such as those disclosed in U.S. Pat. No. 6,491,708 to Madan, et al. attempt to provide a more uniform distribution across individual PZTs and through the PZT stack. One such disclosed embodiment includes providing a bolt head that is substantially equal to the diameters of the individual PZTs. A second disclosed embodiment provides for an aft end bell having a first contact surface and a second contact surface, where the contact area of the second contact surface is less than the surface area of the first contact surface. Rather than applying pressure to the PZT stack at the central bore of the bolt hole, as has been provided in previous devices, the disclosed embodiment transfers the applied pressure to a location offset from the central bore. The Madan patent discloses an improvement in Finite Element Analysis (FIG. 3) over prior designs, such as, for example, the pressure distribution illustrated in FIG. 2, yet may require the use of non-standard components.

FIG. 2 illustrates a prior art plane 10 defined by points 12, 14, 16, and 18 illustrating an example of a Finite Element Analysis for conventional transducer designs. FIG. 2a illustrates that plane 10 is a plane extending radially from the central axis of transducer assembly 82, excepting the bore, and extends longitudinally from the most proximal surface of the transduction portion 90 to the most distal surface of the transduction portion 90. FIG. 3 illustrates a Finite Element Analysis of U.S. Pat. No. 6,491,708 to Madan, et al. showing an improved uniform pressure distribution over a transduction portion plane 20. Transduction portion plane 20 corresponds to plane 10 and illustrates an improved uniform pressure distribution across the proximal surface of the transduction portion as is shown between points 22 and 24.

Non-uniform pressure across the r and z axes may reduce transducer efficiency and may lead to high heat generation. This limitation becomes acutely critical in temperature-limited applications. In temperature-limited applications, the reduced efficiency translates into higher heat generation in the transducer and reduced maximum output. Further, non-uniform pressure limits the magnitude of compression and therefore limits the power capability of the transducer.

There is a need, therefore, for an ultrasonic transducer provided with standard components that exhibits substantially uniform compressive stresses across each PZT and throughout the PZT stack to reduce heat generation and increase power output efficiency.

SUMMARY OF THE INVENTION

Embodiments in accordance with the present invention are directed to ultrasonic transducer assemblies and, more particularly, to transducer assemblies of the composite or sandwich type incorporating a deformable pressure element. Embodiments of the present invention are directed to ultrasonic devices having a transducer assembly adapted to vibrate at an ultrasonic frequency in response to electrical energy. The transducer assembly includes a stack of alternating positive and negative electrodes and piezoelectric elements in an alternating relationship with the electrodes. A mounting device having a first end and a second end is adapted to receive ultrasonic vibration from the stack and to transmit the ultrasonic vibration from the first end to the second end of the mounting device. A bolt including a head and a shaft is configured to threadedly engaged with the mounting device. The transducer assembly further includes a deformable pressure element having a substantially central opening larger than the shaft, the opening configured to permit insertion of the shaft therethrough, the deformable pressure element having a convex side facing the bolt head and a concave side facing the stack in a non-deformed state, the deformable pressure element, in a deformed state, applying compression forces to the stack based on the deformation.

In other embodiments, the deformable pressure element includes a surface area, in its deformed state, substantially equivalent to the surface area of an individual piezoelectric element. In other embodiments the deformable pressure element includes a first and second beveled surface defining the concave side. In other embodiments the deformable pressure element is annular in shape.

Further embodiments of the present invention are directed to ultrasonic surgical devices including a transducer assembly adapted to vibrate at an ultrasonic frequency in response to electrical energy. The transducer assembly includes alternating annular positive and negative electrodes and annular piezoelectric elements in alternating relationship with the electrodes to form a stack having a longitudinal axis. A mounting device includes a first end and a second end, the mounting device adapted to receive ultrasonic vibration from the stack and to transmit the ultrasonic vibration form the first end to the second end of the mounting device. A bolt having a head and a shaft is threadedly engaged with the mounting device. A deformable pressure element includes a substantially central opening larger than the shaft, the opening configured to permit insertion of the shaft therethrough, the deformable pressure element having a convex side facing the bolt head and a concave side facing the stack in a non-deformed state, the deformable pressure element, in a deformed state, applying compression forces to the stack based on the deformation. The ultrasonic surgical device includes a transmission rod having a first end and a second end, the transmission rod adapted to receive ultrasonic vibration form the transducer assembly and to transmit the ultrasonic vibration from the first end to the second end of the transmission rod. An end effector having a first end and a second end is adapted to receive the ultrasonic vibration from the transmission rod and to transmit the ultrasonic vibration from the first end to the second end of the end effector.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

The features of the invention may be set forth with particularity in the appended claims. The invention itself, however, both as to organization and methods of operation, together with further objects and advantages thereof, may best be understood by reference to the following description, taken in conjunction with the accompanying drawings in which:

Figure 1:
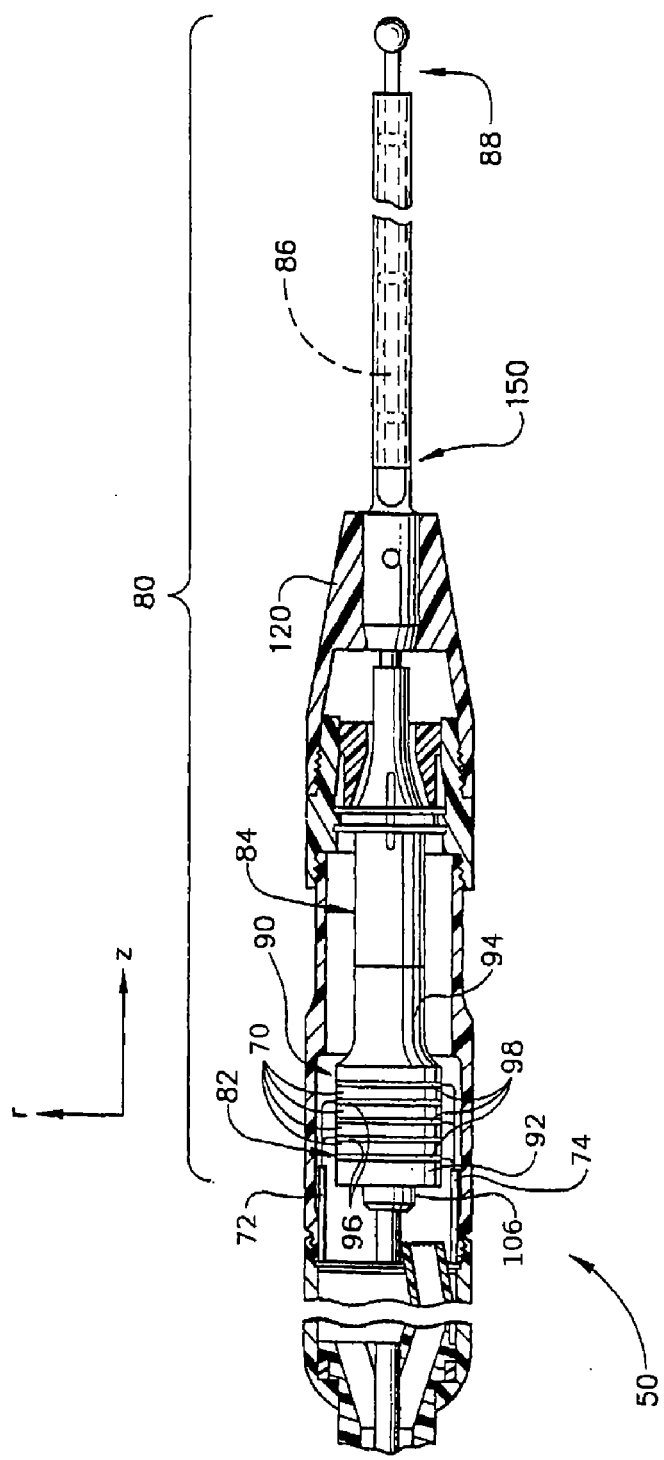
FIG. 1 is a side view of an acoustic or transmission assembly for conventional transducer designs.
Figure 2:
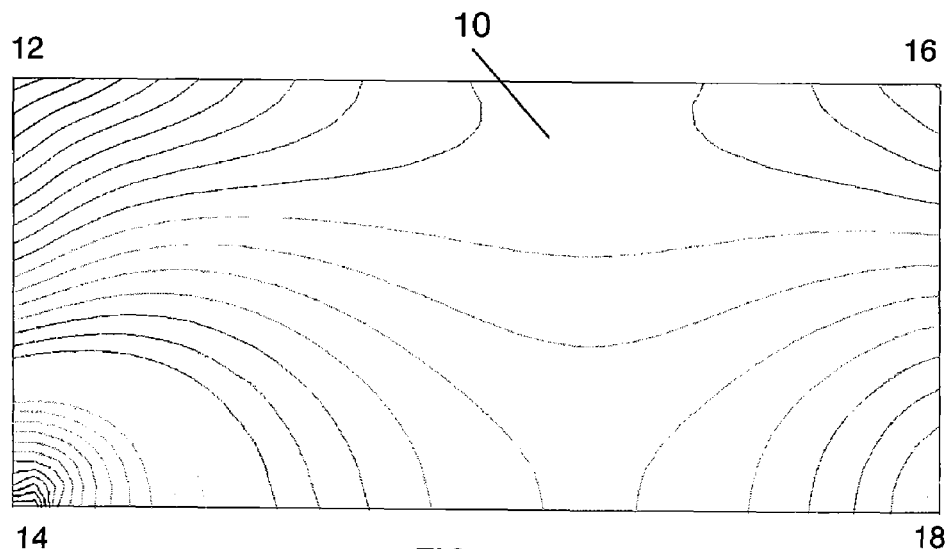
FIG. 2 is a graph of a prior art plane illustrating an example of a Finite Element Analysis for conventional transducer designs.
Figure 2A:
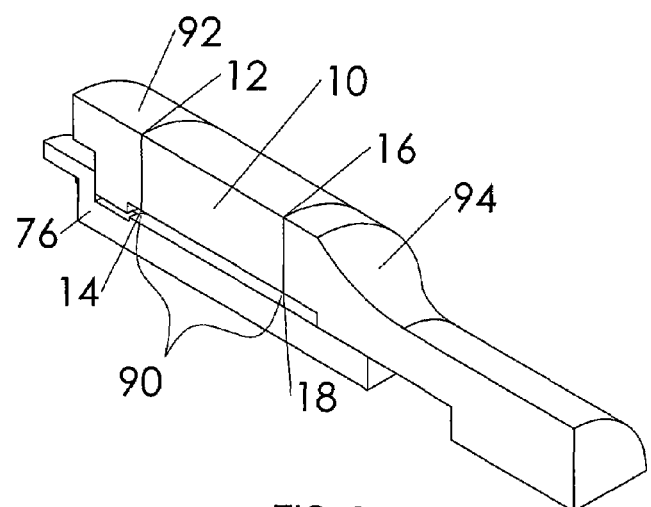
FIG. 2a is a perspective view of a plane extending radially from the central axis of a transducer assembly.
Figure 3:
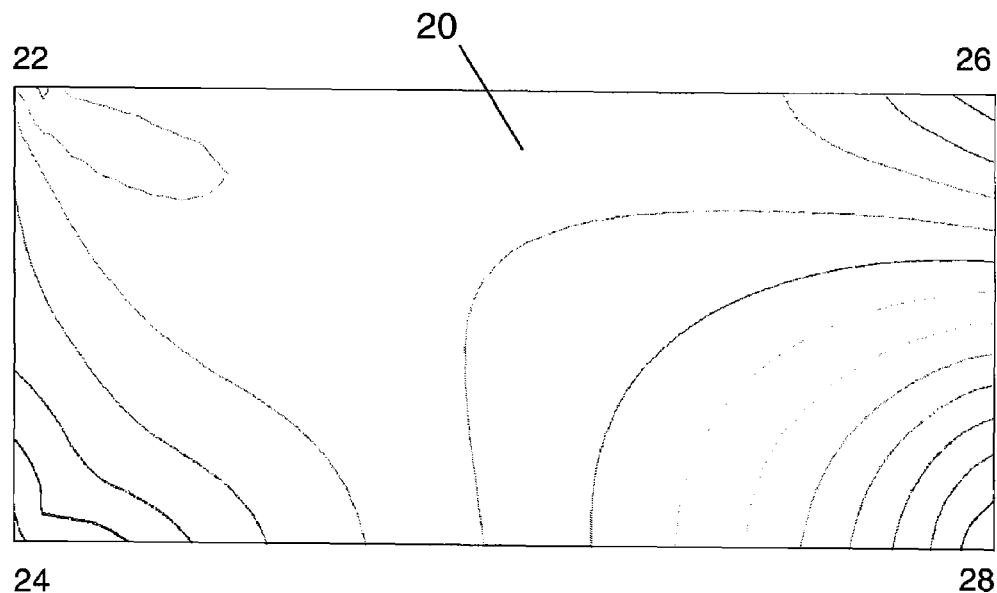
FIG. 3 is a graph of the Finite Element Analysis of U.S. Pat. No. 6,491,708 to Madan, et al. showing an improved uniform pressure distribution over a transduction portion plane.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE PREFERRED EMBODIMENT

Before explaining the present invention in detail, it should be noted that the invention is not limited in its application or use to the details of construction and arrangement of parts illustrated in the accompanying drawings and description. Rather, the illustrative embodiments of the invention may be implemented or incorporated in other embodiments, variations, and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

Figure 4:
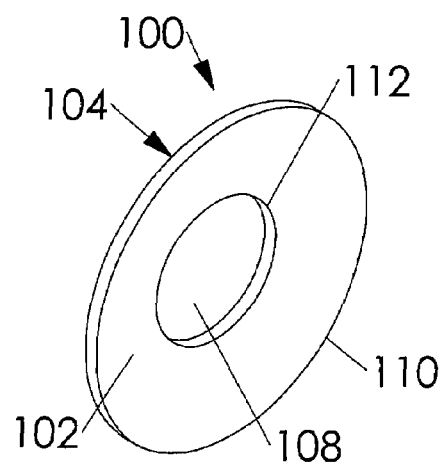
FIG. 4 is a perspective view of one embodiment of a deformable pressure element in accordance with embodiments of the present invention.

FIG. 4 illustrates one embodiment of a deformable pressure element 100 in accordance with the present invention. Deformable pressure element 100 may be, for example, a deformable concave disk having a first contact surface 102, a second contact surface 104, an outer perimeter 110, and an inner perimeter 112. Deformable pressure element 100 may further include a central bore 108 which may be adapted to receive a bolt.

Figure 5:
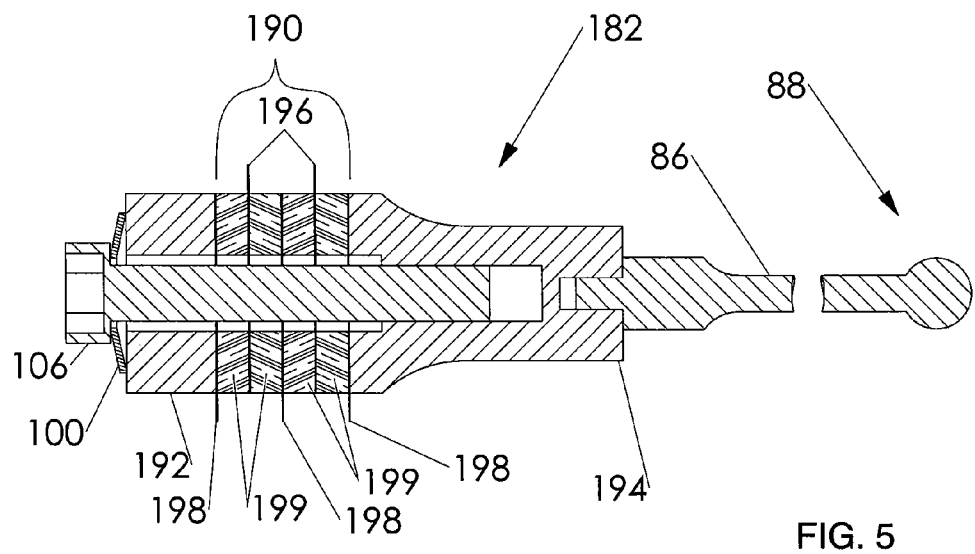
FIG. 5 is a side view of one embodiment of the deformable pressure element incorporated with a transducer assembly shown in initial assembled form in accordance with embodiments of the present invention.

FIG. 5 illustrates one embodiment of the deformable pressure element 100 incorporated with a transducer assembly 182 shown in initial assembled form. Transducer assembly 182 may include, for example, a first resonator or aft end bell 192, a transduction portion 190, and a second resonator or fore end bell 194. The transducer assembly may be, for example, an integral number of one-half system wavelengths (Nλ/2) in length.

The distal end of the first resonator 192 may be connected to the proximal end of transduction portion 190. The first and second resonators 192 and 194 may be, for example, constructed from any suitable material including, but not limited to, titanium, aluminum, or steel. The first and second resonators 192 and 194 may have a length determined by a number of variables, including the thickness of the transduction portion 190, the density and modulus of elasticity of material used in the resonators 192 and 194, and the fundamental frequency of the transducer assembly 182.

The transduction portion 190 of the transducer assembly 182 may include a piezoelectric section (PZTs) of alternating positive electrodes 196 and negative electrodes 198, with piezoelectric elements 199 alternating between the electrodes 196 and 198. The piezoelectric elements 199 may be fabricated from any suitable material, such as, for example, lead zirconate-titanate, lead meta-niobate, lead titanate, or ceramic piezoelectric crystal material. Each of the positive electrodes 196, negative electrodes 198, and piezoelectric elements 199 may have a bore extending through the center. The positive and negative electrodes are electrically coupled to wires (not shown). The wires may transmit signals from a generator (not shown) to the electrodes 196 and 198 as is commonly known in the art.

The piezoelectric elements 199 may be energized in response to the electrical signal supplied from the generator to produce an acoustic standing wave in the acoustic assembly, such as, for example, the acoustic assembly 80 of FIG. 1. The electrical signal causes disturbances in the piezoelectric elements 199 in the form of repeated small displacements resulting in large compression forces within the material. The repeated small displacements cause the piezoelectric elements 199 to expand and contract in a continuous manner along the axis of the voltage gradient, producing high frequency longitudinal waves of ultrasonic energy. The ultrasonic energy is then generally transmitted through the acoustic assembly to an end effector.

The piezoelectric elements 199 may be held in compression between the first and second resonators 192 and 194 by a compression element or bolt 106. The bolt 106 may have, for example, a head, a shank, and a threaded distal end. The bolt 106 may be inserted through the bore 106 of the deformable pressure element 100, through the proximal end of the first resonator 192 through the bores of first resonator 192, the electrodes 196 and 198, and the piezoelectric elements 199. The threaded distal end of the bolt 106 may be screwed into a threaded bore in the proximal end of second resonator 194.

In one embodiment of the present invention, the bolt 106 may be a standard bolt characteristically used in transducer assemblies. However, any suitable compression means may be used in accordance with the present invention. The distal surface of the head of the bolt 106 may contact the second contact surface 104 of the deformable pressure element 100. The first contact surface 102 may be placed in contact with the distal surface of the first resonator 192. Shown in FIG. 5 in the initial assembled form, the outer perimeter 110 of the deformable pressure element 100 may contact the proximal surface of the first resonator 192. The inner perimeter 112 of the deformable pressure element 100, at about the central bore 108, may contact the distal surface of the bolt 106.

Figure 6:
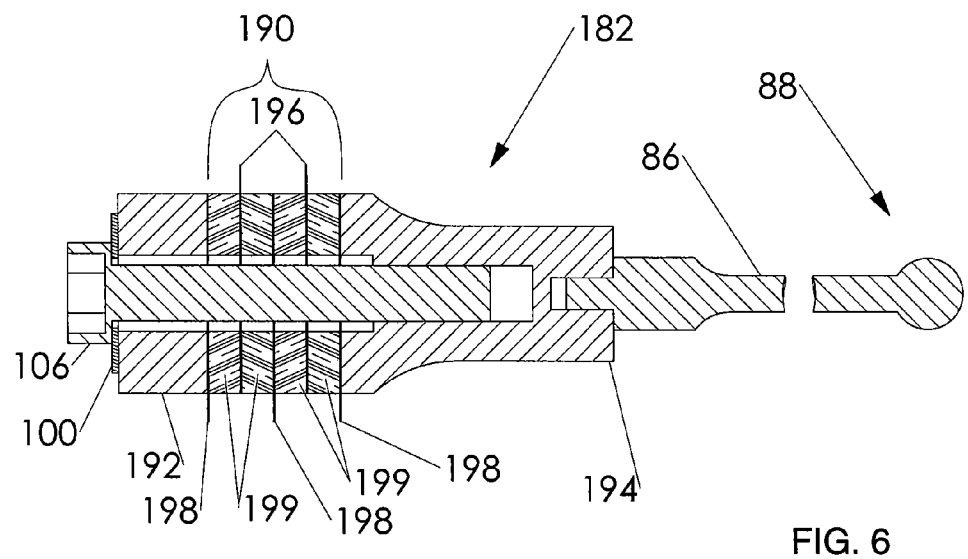
FIG. 6, is a side view illustrating threading the distal portion of the bolt into the corresponding threaded portion of the second resonator to compress the deformable pressure element in accordance with embodiments of the present invention.

In one embodiment, as depicted in FIG. 6, threading the distal portion of the bolt 106 into the corresponding threaded portion of the second resonator 194 may compress the deformable pressure element 100 thereby, for example, driving the deformable pressure element 100 substantially parallel to the proximal surface of the first resonator 192. When bolt 106 is loaded, pressure may be applied to the proximal surface of the first resonator 192 in multiple locations including for example, at the outer perimeter and at the inner perimeter of the deformable pressure element 100. By applying pressure to multiple locations along the proximal surface of first resonator 192, pressure variations within the PZT stack may be reduced. Additionally, applying pressure at multiple locations may allow the pressure variations applied to the PZT stack to be tuned depending on the configuration and placement of the outer perimeter and the inner perimeter of the deformable pressure element 100. Furthermore, the present invention may reduce the pressure variation in the PZT stack by incorporating standard components, such as an off-the-shelf bolt 106, washer 100, or first end resonator 192, which may reduce the cost of providing highly efficient medical devices.

Figure 7:
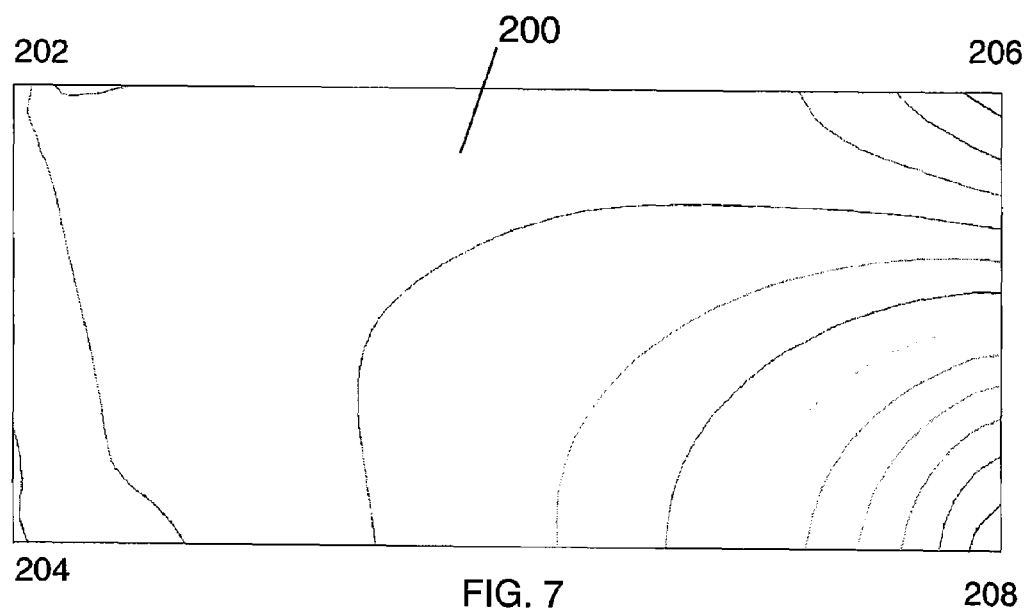
FIG. 7 is a graph of a Finite Element Analysis in accordance with embodiments of the present invention.
Figure 7A:
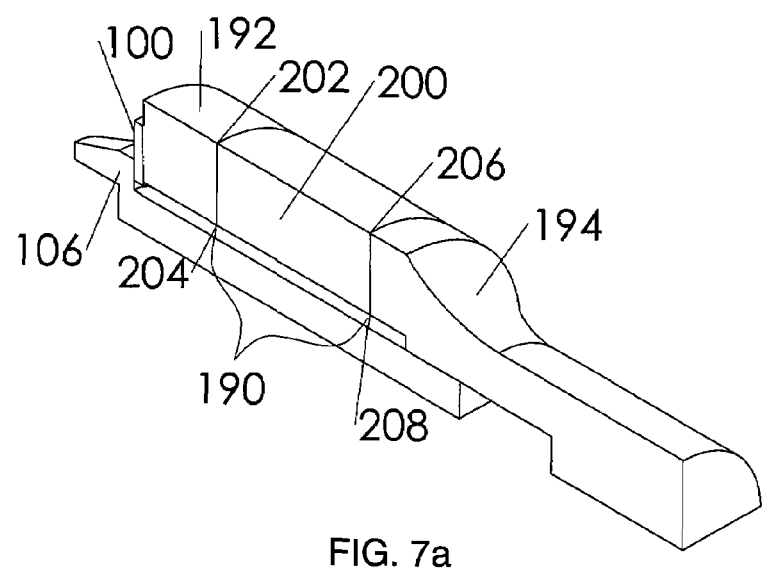
FIG. 7a is a perspective view of an embodiment having the plane extending radially from the central axis in accordance with embodiments of the present invention.

The embodiment disclosed in FIG. 5 may, for example, display a plane 200 (as shown in FIG. 7) illustrating, for example, a Finite Element Analysis in accordance with the present invention. FIG. 7a illustrates one embodiment of the plane 200 extending radially from the central axis, excepting the bore, and extending longitudinally from the proximal surface of transduction portion 190 to the distal surface of the transduction portion 190. Plane 200 includes points 202 and 204, representing the planar proximal surface of the transduction portion 190. Referring to FIGS. 5, 7, and 7a, by incorporating the deformable pressure element 100 into an existing transducer assembly having a standard bolt 106 and first resonator 192, the present invention may reduce the amount of pressure variation across the proximal surface of the transduction portion 190 as compared to conventional transducer assemblies. By combining a reduction of pressure variation, as compared to many conventional instruments, with the low cost associated with the use of standard components, the present invention may provide users with a cost-effective and efficient medical device.

Figure 8:
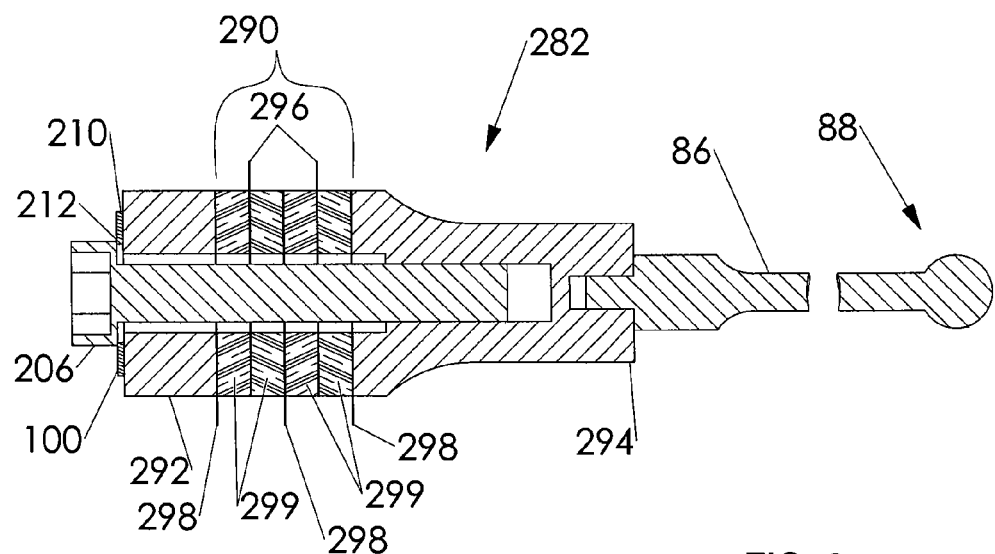
FIG. 8 is a side view of another embodiment of the deformable pressure element in accordance with embodiments of the present invention, where the outer perimeter has a smaller diameter, with respect to the central axis, than the outer diameter of first resonator.
Figure 9:
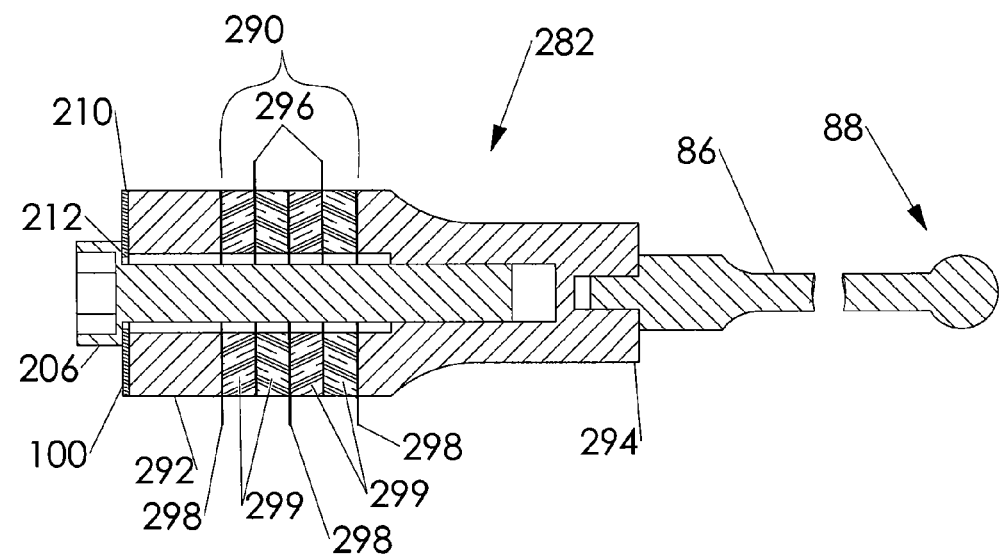
FIG. 9 is a side view of a further embodiment of the deformable pressure element in accordance with embodiments of the present invention, where the outer perimeter has substantially the same diameter.
Figure 10:
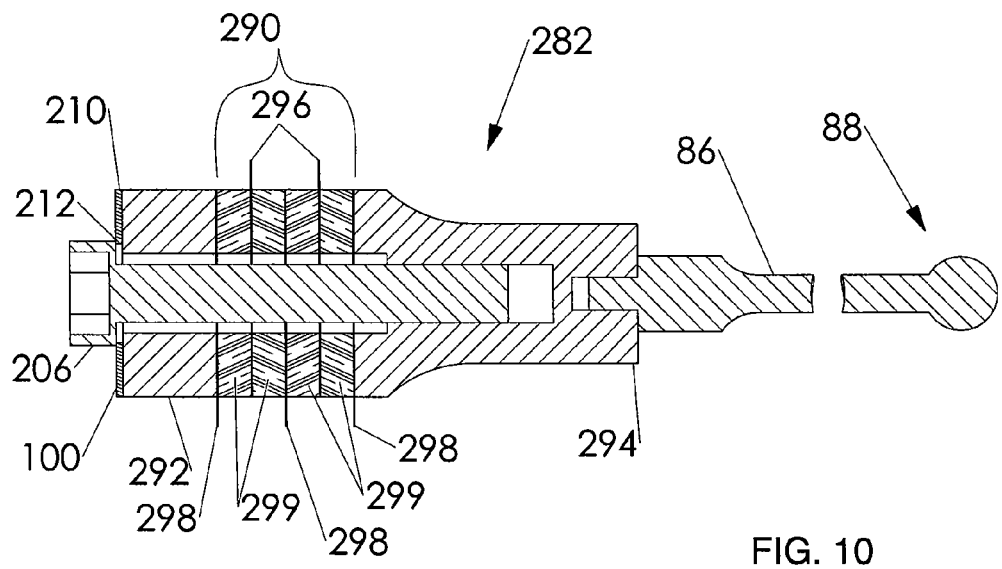
FIG. 10 is a side view of another embodiment of the deformable pressure element in accordance with embodiments of the present invention, where the diameter of the outer perimeter is substantially equal to the diameter of the outer perimeter of the first resonator.

As will be readily apparent to one of ordinary skill in the art from the teachings herein, the deformable pressure element 100 may be dimensioned with any suitable outer perimeter 110 and inner perimeter 112. For example, FIGS. 8, 9, and 10 disclose embodiments of deformable pressure element 100 depicted in the loaded form. FIG. 8 discloses one embodiment of the deformable pressure element 100, where the outer perimeter 210 has a smaller diameter, with respect to the central axis, than the outer diameter of first resonator 292, and the inner perimeter has a larger diameter than the diameter of the bore. FIG. 9 discloses one embodiment of the deformable pressure element 100, where the outer perimeter 210 has substantially the same diameter, measured from the from the central axis, as the outer diameter of the first resonator 292, and the inner perimeter 212 has a smaller diameter than the bore of first resonator 292. FIG. 10 discloses one embodiment of the deformable pressure element 100, where the diameter of the outer perimeter 210 is substantially equal to the diameter of the outer perimeter of the first resonator 292, measured from the central axis, and the inner diameter 210 is larger than the diameter of the bore of the first resonator 292. The illustrated embodiments are disclosed by way of example only and are not intended to limit the scope of the invention. The present invention includes the configuration of deformable pressure element 100 to contact at least two points on the proximal surface of first resonator 192 at any suitable location for reducing pressure variation.

Figure 11:
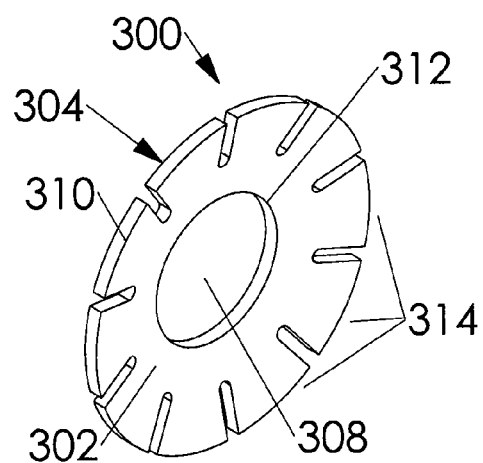
FIG. 11 is a perspective view of a further embodiment of a deformable pressure element in accordance with embodiments of the present invention having a first contact surface and a second contact surface.

FIG. 11 illustrates a further embodiment of a deformable pressure element 300 having a first contact surface 302 and a second contact surface 304. The deformable pressure element 300 may also be provided with an outer perimeter 310, an inner perimeter 312, and a bore 308. In one embodiment, the deformable pressure element 300 is crenelated and may include multiple projections 314. The multiple projections 314 may reduce the stiffness of the deformable pressure element 300 that may be preferable in certain medical devices. The present invention includes using any suitable deformable material, with any suitable spring coefficient, configured in any suitable shape, to provide users with a desirable level of pressure uniformity and spring coefficient. For example, the deformable pressure element 300 may be titanium, steel, or any other suitable material. The deformable pressure element 300 may also be any suitable shape. In further embodiments of the present invention, at least two deformable pressure elements 300 may be stacked between the bolt 106 and the first resonator 292, at least one deformable pressure element 300 may be placed between second resonator 294 and the distal end of the transducer portion 290, and/or at least one deformable pressure element may be placed between the piezoelectric elements 199.

Figure 12:
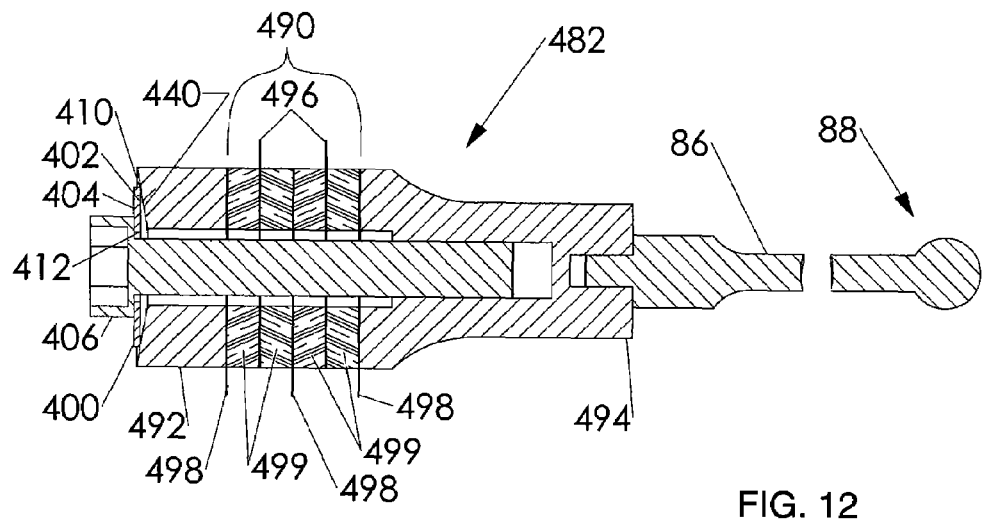
FIG. 12 is a side view of a further embodiment of a deformable pressure element in accordance with embodiments of the present invention having a first contact surface and a second contact surface.

FIG. 12 illustrates a further embodiment of a deformable pressure element 400 having a first contact surface 402 and a second contact surface 404. The deformable pressure element 400 may also be provided with an outer perimeter 410 and an inner perimeter 412. Second contact surface 404 may contact the bolt 406. In one embodiment of the present invention, first contact surface 402 may contact at least two points on the first resonator 492 by providing the first resonator 492 with a concave proximal surface 440 into which first contact surface 402 is driven. In one embodiment, when unloaded, the deformable pressure element 400 may be planar in configuration where, upon loading, the deformable pressure element 400 may be driven parallel to the concave proximal surface 440. Applying pressure to deformable pressure element 400 may drive the deformable pressure element 400 into the convex proximal surface 440, thereby applying pressure at, for example, the outer perimeter 410 and the inner perimeter 412. Applying pressure to at least two points on the proximal surface of the first resonator 492 may reduce the pressure variation within the PZT and may increase the efficiency of instruments constructed in accordance with the present invention.

Figure 13:
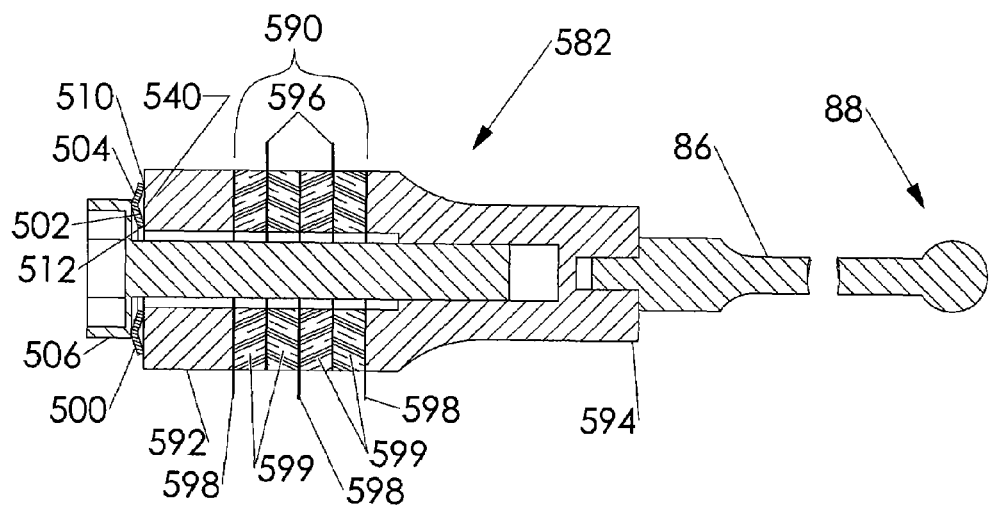
FIG. 13 is a side view of a further embodiment of a deformable pressure element in accordance with embodiments of the present invention that may apply pressure to the proximal surface of first resonator at three points.

FIG. 13 illustrates a further embodiment of a deformable pressure element 500 that may apply pressure to the proximal surface of first resonator 592 at three points. Applying pressure at multiple points may further decrease pressure variation across the Langevin Stack. For example deformable pressure element 500 may include a first contact surface 502 and a second contact surface 504. The deformable pressure element 500 may also include an outer perimeter 510, an inner perimeter 512 and, when unloaded, a concave portion 520. Second contact surface 504 may contact the bolt 506. When pressure is applied to the second contact surface 502 by tightening the bolt 506, the first contact surface 502 of the deformable pressure element 500 may be driven against the proximal surface of the first resonator 592. Tightening the bolt 506 may apply pressure to the first resonator at the outer perimeter 510 and the inner perimeter 512 of deformable pressure element 500. Additionally, applying pressure may compress the concave portion 520 of the deformable pressure element 500, thereby providing a third contact point at the nadir, or deepest portion of the concavity. Providing multiple contact points may increase pressure uniformity throughout the Langevin stack. The illustrated embodiments are illustrated by way of example only and are not intended to limit the scope of the invention. For example, a deformable pressure element may be provided with multiple concavities permitting pressure to be applied at any suitable number of points.

Thus, the described embodiments are to be considered in all aspects only as illustrative and not restrictive, and the scope of the invention is, therefore, indicated by the appended claims rather than the foregoing description. All changes that come within the meaning and range of equivalency of the claims are to be embraced within their scope.

What is claimed is:

1. An ultrasonic surgical device comprising:
    a transducer assembly adapted to vibrate at an ultrasonic frequency in response to electrical energy, the transducer assembly comprising:
    alternating annular positive and negative electrodes and annular piezoelectric elements in alternating relationship with the electrodes to form a stack having a longitudinal axis;
    a mounting device having a first end and a second end, the mounting device adapted to receive ultrasonic vibration from the stack and to transmit the ultrasonic vibration form the first end to the second end of the mounting device;
    a bolt comprising a head and a shaft, the shaft threadedly engaged with the mounting device; and
    a deformable pressure element comprising a substantially central opening sized to permit insertion of the shaft therethrough, the deformable pressure element having a convex side facing the bolt head and a concave side facing the stack in a non-deformed state, the deformable pressure element, in a deformed state, applying compression forces to the stack based on the deformation;
    a transmission rod having a first end and a second end, the transmission rod adapted to receive ultrasonic vibration form the transducer assembly and to transmit the ultrasonic vibration from the first end to the second end of the transmission rod; and
    an end effector having a first end and a second end, the end effector adapted to receive the ultrasonic vibration from the transmission rod and to transmit the ultrasonic vibration from the first end to the second end of the end effector.

2. The device of claim 1 wherein the deformable pressure element comprises a surface area, in its deformed state, substantially equivalent to the surface area of an individual piezoelectric element.

3. The device of claim 1 wherein the deformable pressure element comprises a first and second beveled surface defining the concave side.

4. The device of claim 1 wherein the deformable pressure element is annular in shape.

5. The device of claim 1 wherein the deformable pressure element is substantially annular in shape comprising an outer circular edge, the deformable pressure element comprising a plurality of slits extending inwardly from the outer circular edge toward the substantially central opening.

6. The device of claim 1 wherein the deformable pressure element is substantially annular in shape comprising an outer circular edge a first and second beveled surface defining the concave side, the deformable pressure element comprising a plurality of slits extending inwardly from the outer circular edge toward the substantially central opening.

* * * * *